US011662298B1

(12) United States Patent
Fontaine et al.

(10) Patent No.: US 11,662,298 B1
(45) Date of Patent: May 30, 2023

(54) SYSTEM FOR ELEVATED TEMPERATURE, HIGH PRESSURE ACCELERATED LIFE TESTING USING SEAWATER

(71) Applicant: University of Rhode Island Board of Trustees, Kingston, RI (US)

(72) Inventors: Dillon T. Fontaine, North Smithfield, RI (US); Anthony D. Marshall, Bristol, RI (US); Arun Shukla, Saunderstown, RI (US)

(73) Assignee: University of Rhode Island Board of Trustees, Kingston, RI (US)

( * ) Notice: Subject to any disclaimer, the term of this patent is extended or adjusted under 35 U.S.C. 154(b) by 324 days.

(21) Appl. No.: 17/079,027

(22) Filed: Oct. 23, 2020

Related U.S. Application Data

(60) Provisional application No. 62/925,124, filed on Oct. 23, 2019.

(51) Int. Cl.
*G01N 17/00* (2006.01)
*G01N 33/44* (2006.01)

(52) U.S. Cl.
CPC ........... *G01N 17/002* (2013.01); *G01N 33/44* (2013.01)

(58) Field of Classification Search
CPC .................................................. G01N 17/002
USPC ......................................................... 73/865.6
See application file for complete search history.

(56) References Cited

U.S. PATENT DOCUMENTS

| 2,696,105 | A | * | 12/1954 | Mackas | G01N 3/30 73/12.09 |
| 3,376,660 | A | * | 4/1968 | Mcginnis | G09B 23/28 600/16 |
| 3,877,312 | A | * | 4/1975 | Audet | G01N 33/36 73/865.6 |

(Continued)

FOREIGN PATENT DOCUMENTS

DE 3317782 A1 * 11/1984

OTHER PUBLICATIONS

ESPACENET Machine Translation of DE 3317782 A1 Which Originally Published on Nov. 22, 1984. (Year: 1984).*

(Continued)

*Primary Examiner* — David A. Rogers
(74) *Attorney, Agent, or Firm* — Peacock Law P.C.; Philip D. Askenazy

(57) ABSTRACT

An accelerated life testing (ALT) system for the pressurization of corrosive media, such as seawater, at high pressures and at elevated temperatures (up to about 70° C.) for extended periods of time. The interior of a pressure vessel is coated in an inert ceramic/epoxy coating that provides adequate corrosion protection from the corrosive media. A fabric reinforced nitrile diaphragm separates the corrosive media from hydraulic actuating media, such as oil. The hydraulic actuating media is pressurized, which deforms the diaphragm into the corrosive media, thereby increasing the pressure. The diaphragm and supplementary flouroelastomer seals isolate the corrosive media from pressure generating, monitoring, and safety equipment. The temperature of the entire vessel and contents is maintained by complete immersion in a heated, filtered water bath. The system is particularly useful for ALT experiments on components intended (Continued)

for sea floor and long term deep ocean environment operations at about 6000 psi (41.4 MPa).

22 Claims, 12 Drawing Sheets

(56) References Cited

U.S. PATENT DOCUMENTS

| | | | | |
|---|---|---|---|---|
| 4,479,378 | A * | 10/1984 | Malakhoff | G01M 10/00 73/35.14 |
| 4,495,809 | A * | 1/1985 | Higginbotham | G01M 10/00 73/35.14 |
| 6,298,714 | B1 * | 10/2001 | Courtray | B30B 9/22 73/73 |
| 6,863,123 | B2 * | 3/2005 | Wang | F25D 3/10 374/57 |
| 8,800,353 | B2 * | 8/2014 | Ng | G01N 13/04 73/866 |
| 9,662,210 | B2 * | 5/2017 | Dingmann | A61F 2/2472 |
| 10,264,711 | B2 * | 4/2019 | Dehlsen | H05K 7/20754 |
| 10,656,063 | B2 * | 5/2020 | Daley | G01M 3/24 |
| 11,105,721 | B1 * | 8/2021 | Chen | G01N 3/12 |
| 11,346,746 | B2 * | 5/2022 | Liu | G01M 10/00 |
| 2014/0076029 | A1 * | 3/2014 | Lee | A61F 2/2472 73/37 |
| 2015/0359633 | A1 * | 12/2015 | Dingmann | A61F 2/2472 73/865.6 |
| 2021/0131932 | A1 * | 5/2021 | Serebrinsky | G01N 33/24 |

OTHER PUBLICATIONS

Al-Mazrouee, A., et al., "High Temperature Oxidation of Cr—Mo Steels in the Context of Accelerated Rupture Testing for Creep Life Prediction", J. Pressure Vessel Technol., vol. 129, No. 3, ASME, Aug. 2007, 454-459.

ASTM, "Standard Test Method for Flexural Properties of Polymer Matrix Composite Materials", ASTM D7264 / D7264M-15, ASTM International, West Conshohocken, PA, 2015.

ASTM, "Standard Test Method for Tensile Properties of Polymer Matrix Composite Materials", ASTM D3039 / D3039-M17, ASTM International, West Conshohocken, PA, 2017.

BRP Manufacturing., "Diaphragm Nitrile Specification Sheet-C500", http://brpmfg.com/wp-content/uploads/2016/08/Nitrile-Nylon-Iserted-Diaphrgam-Sheet-C500-PB-Web-10-14-.pdf, accessed Jun. 23, 2021, 2020.

Cartié, D., et al., "The influence of hydrostatic pressure on the interlaminar fracture toughness of carbon/epoxy composites", Composites Part B: Engineering, 37(4-5), 2005, 292-300.

Cerakote, Inc., "Cerakote Elite Series Technical Data Sheet", 2019.

Davies, P., et al., "Composite Cylinders for Deep Sea Applications: An Overview", J. Pressure Vessel Technol., vol. 138, No. 6, ASME, Jul. 18, 2016, 060904-1-8.

Fine, Rana A., et al., "Compressibility of water as a function of temperature and pressure", J. Chem. Phys., vol. 59, No. 10, 1973, 5529-5536.

Guo, J. Q., et al., "An Accelerated Method for Creep Prediction from Short Term Stress Relaxation Tests", J. Pressure Vessel Technol., vol. 138, No. 3, ASME, Jun. 2016, 031401-1-5.

Gupta, S., et al., "Study of dynamic underwater implosion mechanics using digital image correlation", Proc. R. Soc. A., 470:20140576, 2014, 2-17.

Hermida, A., "Deflection of Circular Membrane Under Differential Pressure", NASA Tech Briefs, vol. 22, No. 5 (Abstract only), May 1998.

Humeau, C., et al., "Moisture diffusion under hydrostatic pressure in composites", Materials & Design, 96(July), 19, 2015.

Kishore, et al., "Compression strength of saline water exposed epoxy system containing fly ash particles", Journal of Reinforced Plastics and Composites, 24(15), 2005, 1567-1576.

Le Gac, P.-Y., et al., "Evaluation of Long Term Behaviour of Polymers for Offshore Oil and Gas Applications", Oil & Gas Science and Technology—Revue d'IFP Energies Nouvelles, 70(2),, 2015, 279-289.

Matos, H., et al., "Underwater nearfield blast performance of hydrothermally degraded carbon-epoxy composite structures", Multiscale and Multidisciplinary Modeling, Experiments and Design, 1(1), 2018, 33-47.

Mforsoh, I., "Constitutive compressive behavior of polyurea with exposure to aggressive marine environments", Polymer Testing, 85, 2020.

Papanicolaou, G. C., et al., "Water absorption mechanism and some anomalous effects on the mechanical and viscoelastic behavior of an epoxy system", Journal of Applied Polymer Science, 99(4), 2006, 1328-1339.

Pinto, M., et al., "Experimental Investigation on Underwater Buckling of Thin-Walled Composite and Metallic Structures", J. Pressure Vessel Technol., vol. 138, No. 6, ASME, Jul. 18, 2016, 060905-1-8.

Pinto, M., et al., "Hydrostatic Implosion of GFRP Composite Tubes Studied by Digital Image Correlation", J. Pressure Vessel Technol., vol. 137, No. 5, ASME, Oct. 2015, 051302-1-12.

Sanchez Nacher, L., et al., "Mechanical Properties of Polyester Resins in Saline Water Environments", International Journal of Polymer Analysis and Characterization, 12(5), 2007, 373-390.

Shillings, C., et al., "Experimental and computational investigation of the blast response of Carbon-Epoxy weathered composite materials", Composites Part B: Engineering, 129, 2017, 107-116.

Tucker, W. C., et al., "Moisture Absorption of Graphite / Polymer Composites Under 2000 Feet of Seawater", Journal of Composite Materials, 23(8), 1989, 787-797.

Tucker, W., et al., "The effects of pressure on water transport in polymers", Journal of Composite Materials, 27(8), 1993, 756-763.

Zuo, M., et al., "Fitting Creep-Rupture Life Distribution Using Accelerated Life Testing Data", J. Pressure Vessel Technol., vol. 122, No. 4, ASME, Nov. 2000, 482-487.

* cited by examiner

SYSTEM FOR ELEVATED TEMPERATURE, HIGH PRESSURE ACCELERATED LIFE TESTING USING SEAWATER

CROSS-REFERENCE TO RELATED APPLICATIONS

This application claims priority to and the benefit of the filing of U.S. Provisional Patent Application No. 62/925,124, filed on Oct. 23, 2019, entitled "System for Elevated Temperature, High Pressure Accelerated Life Testing Using Seawater", the specification, appendix, drawings, and claims of which are incorporated by reference.

STATEMENT REGARDING FEDERALLY SPONSORED RESEARCH OR DEVELOPMENT

This invention was made with government support under Contract Nos. N00014-18-1-2641 awarded by the Office of Naval Research. The government has certain rights in the invention.

BACKGROUND OF THE INVENTION

Field of the Invention (Technical Field)

The present invention is related to accelerated life testing for undersea or other components exposed to a process media such as seawater, concentrated acids, and industrial solvents.

Background Art

Note that the following discussion may refer to a number of publications and references. Discussion of such publications herein is given for more complete background of the scientific principles and is not to be construed as an admission that such publications are prior art for patentability determination purposes.

Accelerated life testing (ALT) is a common technique used across industries to test the performance of a design throughout, or in some cases to determine, its service life. Common examples of this include accelerating aging such as corrosion behavior and determining fatigue and creep parameters. It is a simulated method, the first step of which is to determine factors which are thought to degrade performance, such as seawater ingression. Then, specimens that represent the design are exposed to an environment that accelerates the rate at which these factors act; a common application is to raise the temperature of a humidity chamber or water bath to accelerate the rate of corrosion or moisture ingression. This method has been used recently to study the effects of marine environments on polymer and composite structures. The demand for greater operating depths and thus higher working pressures is ever increasing.

"Accelerated" means that a parameter about the operating environment has been modified in the laboratory from its natural or service environment that results in the material or structure responding to laboratory testing after a certain period of time the same way that the material/structure would in its service environment only after a longer period of time. The "acceleration" in ALT is achieved by changing some parameter or parameters of the service environment in order to increase the speed at which the degradation mechanism operates. These variables are the exclusive inputs to an acceleration map; all other aspects of the service environment must be held constant in the test environment (i.e. the control variables). The acceleration map takes the experimental variables as its total inputs and uses these to map exposure time in the laboratory environment to time spent in service. This relationship is often experimentally determined, and when it is, a significant portion of testing time is typically spent determining it. Except in the simplest of cases, it should be assumed to be unique for every material/control variables combination.

The laboratory environments required to perform this new generation of accelerated testing created a unique challenge in procuring or designing a compatible pressure vessel. The required aging times are typically as long as 1000 hours, wherein a pressure hold of up to 41.3 MPa (6000 psi) would need be maintained at temperatures of up to 70° C. This combination of saline media, temperature, and time risks severe corrosion to both the pressure vessel body and the pump, gages, and fittings. Coatings have been researched for the interior of the vessel, but these coatings cannot reliably be used on moving parts such as needle or pressure relief valves, where the extreme sealing pressures required of these devices wears the coatings away after a few uses. This approach is also expensive, and so is using exotic metals such as Monel in the valves and other pressure equipment. This option is too costly and still potentially unreliable, as corrosion may yet attack even these metals after the durations of exposure required by the tests.

Another design uses pressurized nitrogen or another inert gas to fill a small gap of air at the top of the pressure vessel. The pressure is controlled from a remote location by modulating the nitrogen pressure, which by equilibrium induces the same pressure in the underlying fluid region. A benefit of this design is that the pressure generating, monitoring, and relief equipment as well as any valves do not make contact with the fluid, yet by equilibrium, all measurements of pressure made on the gas are guaranteed to coincide with the actual pressure of the fluid. But this design is unsafe at the pressures and volume of an ALT vessel; the energies contained in the gas pocket rival that of 10 grams of TNT. Additionally, vapors of the process media may yet migrate through whatever gas line exists and still corrode equipment. This combination of explosive potential energy combined with the risk of a seized valve or pressure relief rules out inert gas as a pressurizing method.

SUMMARY OF THE INVENTION (DISCLOSURE OF THE INVENTION)

An embodiment of the present invention is a system for pressurizing corrosive media, the system comprising a vessel configured to contain a corrosive media and a test specimen; a flexible diaphragm, wherein a first side of the diaphragm is configured to seal one end of the vessel; a connection assembly configured to transport a pressurizing fluid to a second side of the diaphragm; and a temperature-controlled water bath configured to submerge the vessel. The vessel preferably comprises stainless steel. The interior of the vessel is preferably coated with a ceramic coating, which is preferably a resin-based ceramic thin film coating. One or more hoisting rings configured to receive one or more hooks to lift the vessel into the water bath are preferably attached to the top of the vessel. The system preferably comprises a pump configured to pressurize the pressurizing fluid against the second side of the diaphragm. The pump preferably comprises a pressure release valve and is preferably connected to the connection assembly via a flexible hose. The diaphragm is preferably configured to deform and protrude into the corrosive media when the pressurizing fluid is pressurized by the pump, thereby pressurizing the corrosive media to approximately a same pressure as the pressurized pressurizing fluid. The connection assembly preferably comprises a rupture disc and a pressure sensor. The pressure sensor is preferably connected to the connection assembly via a flexible tube. The diaphragm preferably comprises fabric reinforced nitrile rubber. The pressurizing fluid preferably comprises hydraulic oil. The vessel is preferably cylindrical. The diaphragm is preferably clamped between a flange attached to the vessel and a bottom end cap, the flange and the bottom end cap preferably having diameters greater than a diameter of the vessel. The flange is preferably clampable to the bottom end cap using a plurality of through bolts. The bottom end cap preferably comprises grooves for receiving one or more flouroelastomer O-rings configured to contain the pressurizing fluid between the second side of the diaphragm and the bottom end cap. The system is preferably capable of maintaining the corrosive media at a pressure of approximately 6000 psi and at a temperature greater than approximately 40° C. for more than approximately one month, and more preferably about three months, without corrosive failure of the system. The corrosive media preferably comprises seawater, saline, or salt water. The system is preferably capable of performing accelerated life testing (ALT) of the specimen.

Objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate the practice of embodiments of the present invention and, together with the description, serve to explain the principles of the invention. The drawings are only for the purpose of illustrating certain embodiments of the invention and are not to be construed as limiting the invention. In the drawings.

DETAILED DESCRIPTION OF EMBODIMENTS OF THE INVENTION

Figure 1:
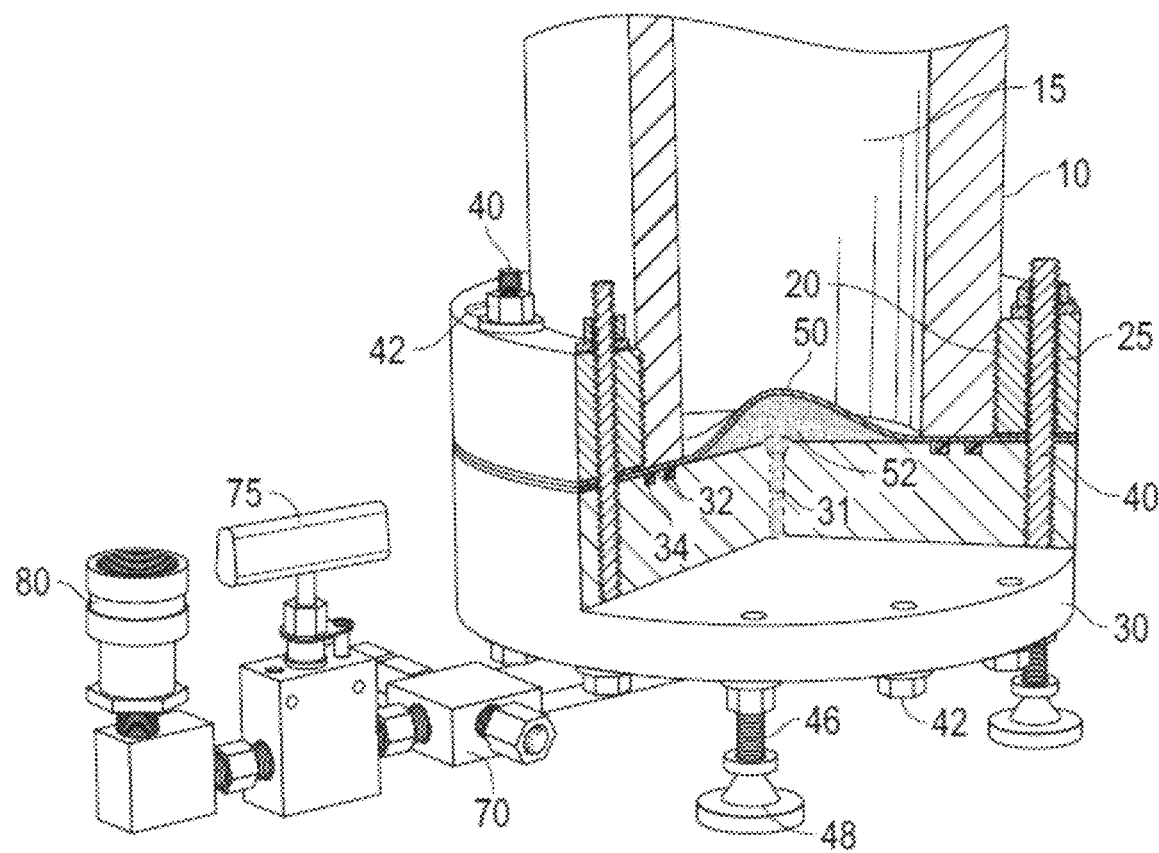
FIG. 1 is a cutaway view of the pressure vessel system of the present invention.
Figure 2:
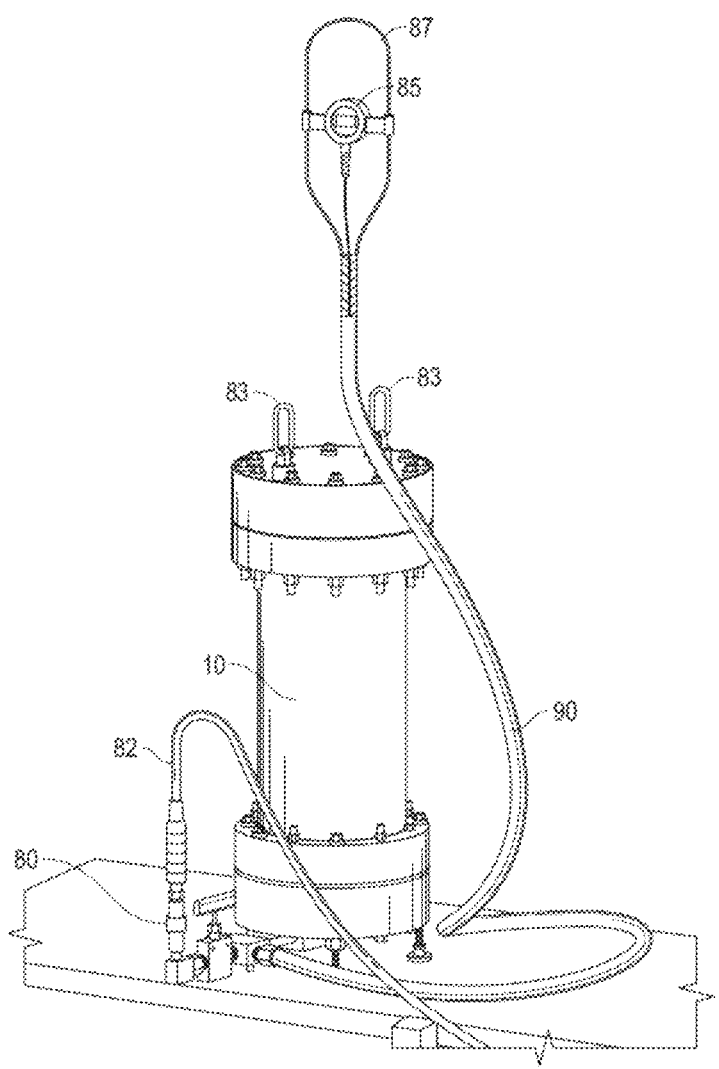
FIG. 2 shows the assembled pressure vessel of the present invention.

Embodiments of the apparatus of the present invention comprise a pressure vessel which contains and pressurizes process media such as seawater (i.e. 3.5% NaCl water) to adjustable pressures up to ocean floor depth pressures (6000 psi). The vessel preferably enables quick access to specimens when conducting certain studies, such as diffusion studies. As shown in FIGS. 1 and 2, the vessel comprises vessel body 10 which encloses containment region 15. The ends of the body preferably comprise external threads 20 to accept flanges 25, and the face of the top end of vessel body 10 is preferably trepanned for an O-ring gland to receive an O-ring used as a face seal between the body and top end cap. The vessel components are preferably stainless steel.

Bottom end cap 30 preferably comprises a concentric tapped first through-hole 31 by which the plumbing from the pump connects. Offset a small distance from this center hole is preferably a plugged second through-hole (not shown) acting as an air bleeder. On the top surface of bottom end cap 30 in the region in contact with the body section are preferably two concentric O-ring grooves 32, 34. Preferably only the innermost ring is sealing; the second trepan serves to concentrate clamping pressure on the diaphragm by reducing the area in contact, thereby providing a better seal.

In use the flanges are threaded onto the body and the top and bottom end caps are fastened to the flanges preferably by bolts 40 that extend through both the flange and corresponding end cup, preferably tightened using nuts 42 at both top and bottom. However, for bottom end cap 30, every third bolt is preferably replaced by a longer bolt 46 which preferably terminates in swiveling adjustable foot 48, which gives the vessel additional ground clearance, for example approximately 3 inches, also enabling the plumbing to attach directly to the bottom of bottom end cap 30.

All surfaces in contact with the process media, for example seawater, including the entire inside cylindrical surface of the body section, the top and bottom end faces of the body including the O-ring gland, and the bottom surface of the top end cap which contacts the face seal and encloses the pressurized volume, are preferably coated with a ceramic coating that can withstand corrosion for at least six months. The coating preferably enables the interior of the vessel to handle many different corrosive liquids directly, including the salt water used in many ALT's, as long as the liquid is chemically compatible with the ceramic coating and type of rubber chosen as the diaphragm and seal materials.

The top end cap is preferably identical to the bottom end cap except without the through-holes, and the top end cap optionally comprises one or more, preferably two, shallow tapped blind holes into which threaded hoisting rings 83 or other fixtures for lifting the vessel are anchored to the top end cap. The assembled vessel may then be lifted by a gantry crane or the like and preferably immersed within a temperature containment drum, preferably filled with clean, filtered water and heated by an insulated, wrap-around heater with automatic temperature control to regulate the temperature of the primary vessel and its contents. In this way, by controlling the temperature of the clean water bath, immersion of the vessel directly holds the pressurized contents at a desired temperature. In some embodiments the temperature can safely be held between the ambient temperature and about 70 degrees Celsius.

The seawater or other near-incompressible media in the pressure vessel is pressurized preferably via means of hydraulic fluid pressure acting against a flexible diaphragm of a chemically resistant material. Hydraulic oil has long-term stability even in high heat, is inert and non-corrosive, and is nearly incompressible making it preferred for high pressure application such as the present invention. The hydraulic oil is pumped preferably via a hand-operated hydraulic pump through a hose and high-pressure piping stem against the lower side of deformable diaphragm 50. Deformable diaphragm 50 separates and isolates the process media (e.g. seawater) from the pressurizing media (the stable hydraulic oil). The hydraulic oil occupies region 52 which expands into containment region 15 causing an approximately equal pressure (except for the diaphragm's resistance to deflection) to develop within containment region 15. Because the pressures are approximately equal, the pressure gauge can be exposed only to the oil and not the corrosive process media. The preferably standard connections on the vessel enable any hydraulic pump to be used. The vessel may not have a separate valve for pressure release, although the design is flexible enough to include one, which means the use of a single-acting pump with integral release valve is preferred. In this configuration, the pressure can be relieved by venting the hydraulic oil, not the process media.

Figure 3:
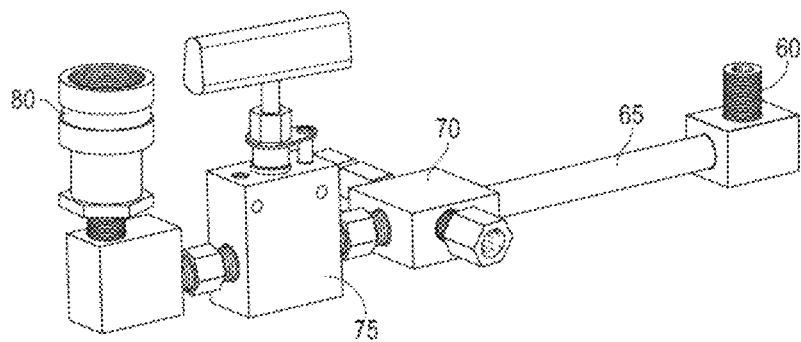
FIG. 3 shows an exemplary plumbing assembly of the present invention.
Figure 4A:
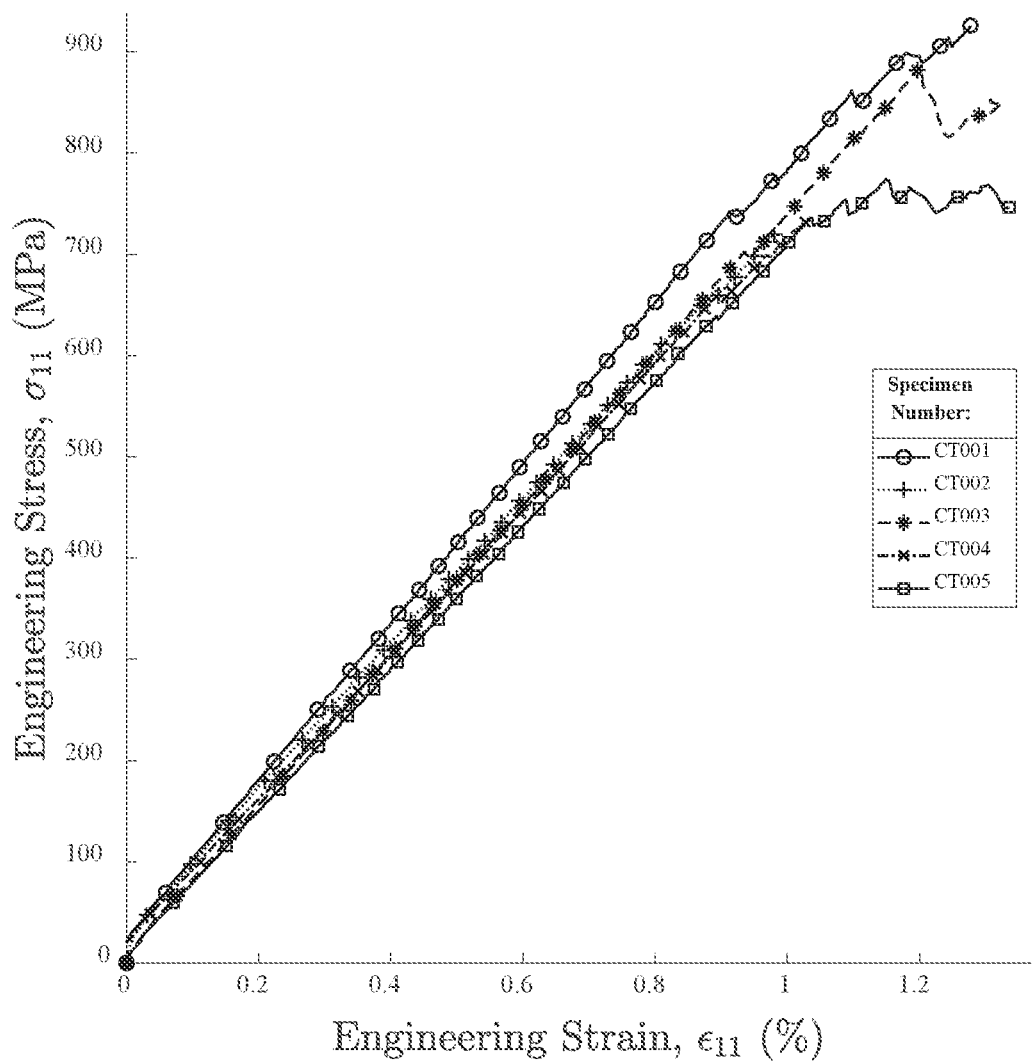
FIG. 4A shows engineering stress-strain curves for quasi-static in-plane tensile tests on an unweathered carbon fiber/epoxy (CFE) specimen.
Figure 4B:
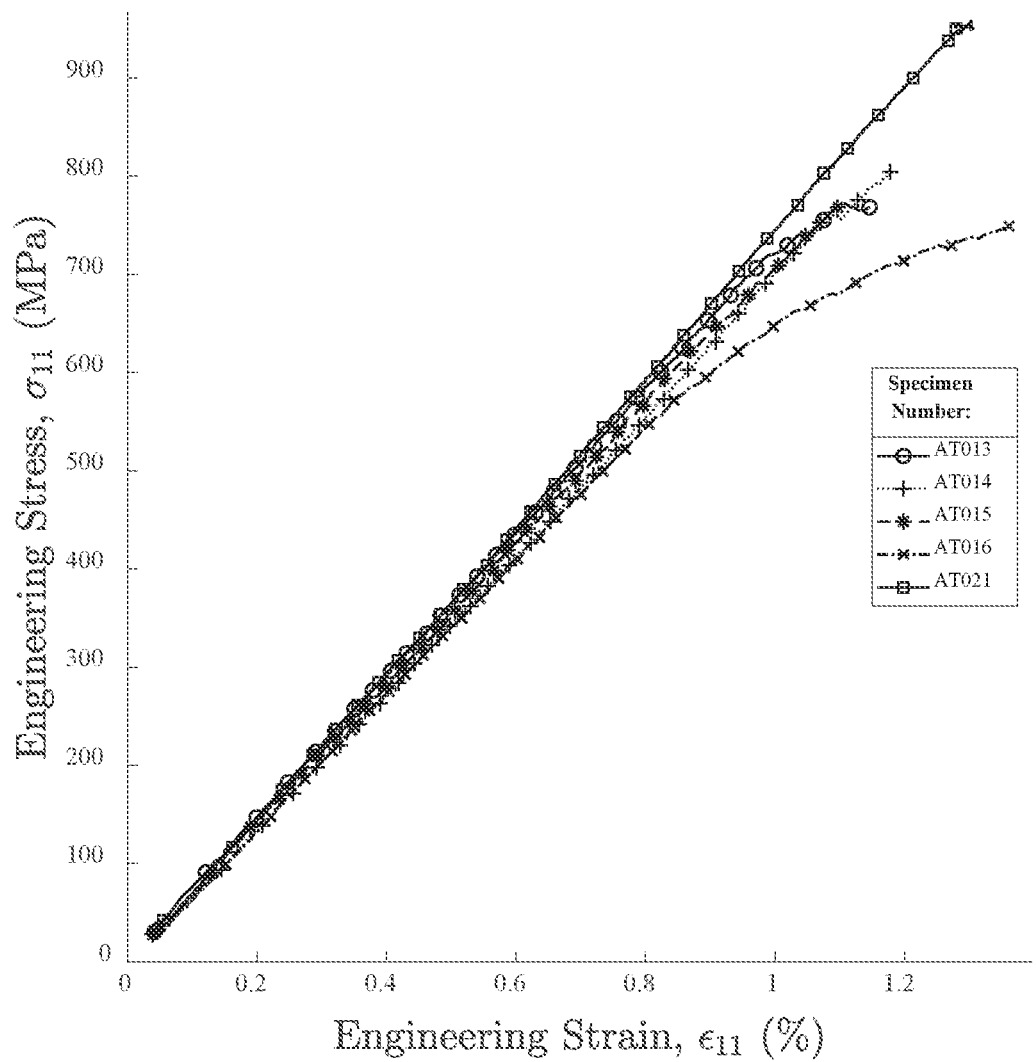
FIG. 4B shows engineering stress-strain curves for quasi-static in-plane tensile tests on a CFE specimen weathered for 14 days at 70° C.
Figure 4C:
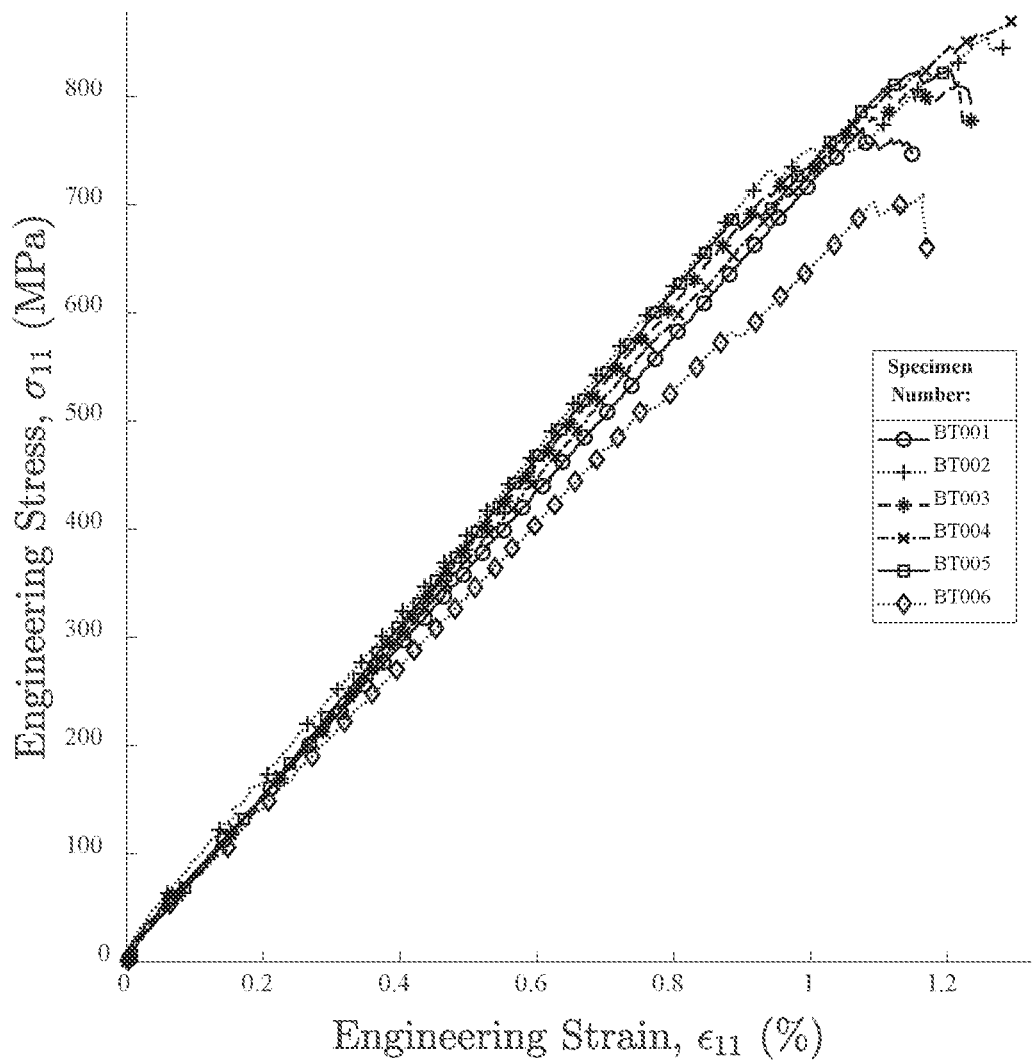
FIG. 4C shows engineering stress-strain curves for quasi-static in-plane tensile tests on a CFE specimen weathered for 24 days at 70° C.
Figure 4D:
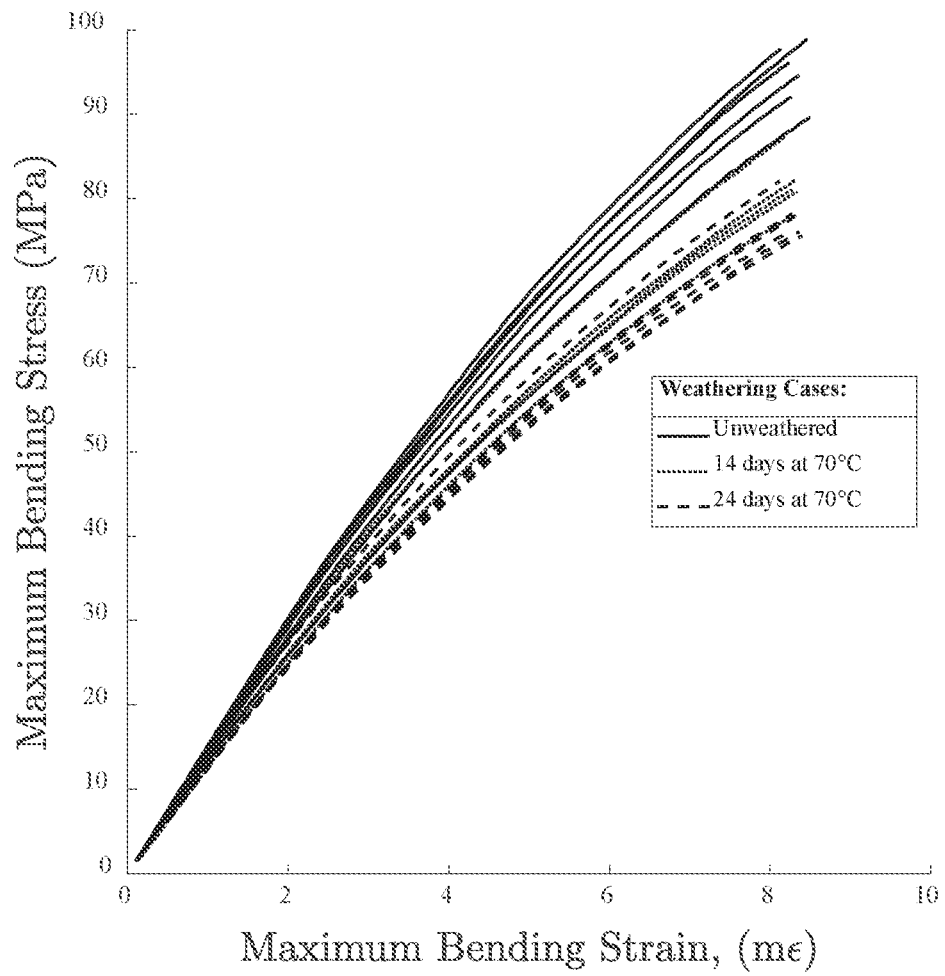
FIG. 4D shows stress-strain curves for three-point bend tests on the specimens of FIGS. 4A-4C.

Flexible elastomeric hydraulic fluid hose 82 connects the pump to the plumbing assembly shown in FIG. 3, which is preferably attached to the vessel at the tapped through-hole 31 at the bottom face of bottom end cap 30. The assembly consists of elbow 60 threaded into the bottom end cap which then routes pipe nipple 65 between the legs of the pressure vessel. Following this is cross 70 into which a pressure transducer is attached to one side and a safety head with a rupture disc is threaded on the other side. The pressure transducer preferably comprises pressure gauge 85 which connects to cross 70 via pressure extension tube 90. The rupture disc is preferably set to burst at a pressure slightly higher than the vessel's maximum allowable working pressure, for example approximately, 41.3 MPa, and well below the design failure pressure. Following the cross is needle valve 75, which serves to fully isolate the pressure vessel, and the plumbing preferably terminates in hydraulic coupler 80 that connects to the hose from the pump. When the pressure vessel is submerged in the water bath, hydraulic fluid hose 82 and pressure extension tube 90 preferably extend out of the containment drum, enabling the pump and pressure gauge 85 to remain dry. Pressure gauge 85 may be hung from hanger loop 87 during use for ease of viewing.

Deformable diaphragm 50 is sealed on the oil side by O-rings 32, 34, as well as by compression in the band of material between the glands. Because some pressure is required to deform the diaphragm into its bell-like shape, the oil pressure is naturally slightly higher than the pressure of the process media, so a gasket style seal is all that is required between deformable diaphragm 50 and the end face of vessel body 10. Deformable diaphragm 50 preferably comprises fabric reinforced rubber such as nitrile rubber because of its good chemical resistance to seawater and other common process media. Nitrile is a common seal material particularly around hydraulic oils, although other rubber types may be used depending on their chemical compatibility with the type of corrosive process media used. Although any fabric may be used, the fabric preferably comprises nylon, which is tolerant to both salt water and oils if the rubber sheet cracks or is otherwise penetrated, thus exposing the cloth. A cloth reinforcement maintains dimensional stability and limits compression set when used in the high-pressure seals of the vessel. Because the diaphragm strains are much less than the through-thickness compression, there is minimal risk of tearing, even at large displacements. Large strain-to-failure of the diaphragm material enables large displaced volumes and high pressures. Other advantages of such a diaphragm are that fatigue is practically non-existent; the diaphragm flows into gaps, forming robust, leakproof seals, and the diaphragm is nearly incompressible (the Poisson effect practically negates diaphragm strains).

Via the thermostat and pressure monitoring equipment, the contents may thus be exposed to the heated and pressurized seawater at an desired pressures and or temperatures unattended for a period of up to six months, or even longer, without damage to operating components of the system that would result in inoperability, thus enabling automated, low cost high pressure accelerated life testing on materials and structures.

Example

A vessel of the present invention was constructed and tested. The vessel body had a wall thickness of about 1.5 inches and the containment region was about 6.0 inches in diameter and about 21.0 inches long. The vessel components were fabricated from AISI 304L stainless steel, which was chosen for its good balance of strength, corrosion resistance, machinability, and creep behavior. A No. 441 O-ring was used as a face seal between the body and top end cap. The top and bottom end caps were each about 12 inches in diameter and about 3.25 inches thick. The concentric through-hole was tapped for a 3/8-18-NPT thread on both ends and the air bleeder through-hole comprised a plugged 1/8-27-NPT thread and was offset about 2 inches from the concentric through-hole. The inner and outer O-rings for sealing the bottom end cap were No. 439 and 444 nitrile rings, respectively. Twelve 1/2-20-UNF Grade 9 bolts were used to seal the bottom end cap to the bottom flange. The vessel was successfully tested to 9000 psi and 75° C., and had a combined opening and closing time of less than five minutes.

The ceramic coating comprised Cerakote Elite Series E190, a resin-based ceramic thin film coating which was chosen primarily for its excellent hardness and corrosion resistance and which has a survivability exceeding 4000 hours in an ASTM B117 salt spray test. The coating was also chosen for its flexibility and adhesion, important concerns when taking thermal expansion and cycling into account, combined with large compressive stresses. The oil pump was an Enerpac P39 hand operated hydraulic pump. The diaphragm was nylon fabric reinforced Buna-N (nitrile) sheet with part number C2500-0125-121 (BRP Manufacturing, Inc., Lima, Ohio), having two cloth plies, a thickness of about 2.98 mm, and an areal density of 3.20 kg/m$^2$. The diaphragm rubber has an ASTM D2000 standard callout of 2BG515A14B14C12E014E034F19, and the diaphragm fabric is a biaxial plain woven, high tensile strength nylon manufactured by DuPont (Wilmington, Del.) having a weight of 373 g/m$^2$.

The average strain on the diaphragm was calculated and the pressure difference between process and pressurizing media domains were estimated as follows. It was assumed that the diaphragm behaves effectively isotropically for small strains, due to the difference in cloth areal density and bulk material areal density. The density of nitrile rubber is approximately 1200 kg/m³, which, when factoring in the thickness of the diaphragm, leads to an areal density of 3.60 kg/m². The areal density of 3.20 kg/m² of the diaphragm, together with the areal density of the cloth of 0.373 kg/m², implies the diaphragm material is nearly 88% nitrile and 12% cloth by volume. Additionally, when considering the cloth is unstressed and not pulled taut within the nitrile, nor are individual fibers taut within each thread, a majority of any applied load at small strains will not have overcome the pre-stress required to fully engage the cloth fibers. Thus it is a fair assumption that at small strains, the material overall behaves much like unreinforced nitrile, which is an isotropic elastomer with typical M100 modulus of 3.00 MPa and a Poisson's ratio of approximately 0.49, typical for elastomers. For a circular diaphragm clamped at its edges and subjected to a pressure difference, the vertical deflection, w, (excursion into the process media) is given by the following equation:

$$w(r) = w_0 \left[1 - \left(\frac{r}{a}\right)^2\right]^2$$

where $w_0$ is the maximum excursion at the center of the diaphragm, r is the radial coordinate from the center, and a is the radius of the clamped boundary. $w_0$ is further given by the following equation:

$$w_0 = \alpha a * \sqrt[3]{\frac{qa}{Eh}}$$

where q is the differential pressure, E is the modulus of elasticity, h is the thickness of the diaphragm, and $\alpha$ is a dimensionless parameter defined in terms of Poisson's ratio, $\upsilon$, as follows:

$$\alpha = \sqrt[3]{\frac{6615(\upsilon^2 - 1)}{2(2791 \upsilon^2 - 4250 \upsilon - 7505)}}$$

For a Poisson's ratio of 0.49, this parameter evaluated to 0.656.

Additionally, the design pressure for the vessel was 41.3 MPa, with a maximum operating temperature of 70° C. Using known values for the compressibility of water at various temperature and pressure combinations, and the definition of bulk modulus K as the reciprocal of compressibility, a conservative average bulk modulus for the water domain across the range of design pressures and temperatures is 2.55 GPa. The volume change, $\Delta V$, of a fluid under pressure is a well-known equation:

$$\Delta V = \frac{V_0 \Delta P}{K}$$

where $V_0$ is the original volume and $\Delta P$ is the change in pressure. Because the vessel is initially at ambient pressure and the design value is relative to this pressure, $\Delta P$ is automatically the design value. Using the dimensions given above for the usable volume of the vessel, this reduction in volume was calculated to be 135 mL. Because the diaphragm is circular and thin, the volume the water compresses by to achieve a certain pressure is equal to the volume contained by the deformed diaphragm shape relative to its initial profile. This amounts to simply the volume of a revolution of the deformed profile about the r=0 axis, given by the following:

$$\Delta V = 2\pi \int_0^a r|w(r)|dr$$

By substituting the first equation into this equation and solving for $w_0$ given the value of $\Delta V$ calculated from Eq. 4, the maximum excursion of the diaphragm was found to be 22.2 mm. The average strain along the radius was obtained by comparing the arc-length of half the deformed shape to the initial value of simply a. Doing so resulted in an increase from 76.2 mm to 80.0 mm, or a 5% average radial strain. This value is low enough in comparison to the failure strains of either material to conclude that the diaphragm should not tear from membrane strains and is also of a magnitude where the stiffness assumptions hold. Additionally, by substituting the maximum excursion value into Eq. 3 and solving for q, which is a good estimator of the pressure drop between the process and pressurizing domains, a value of 10.3 kPa was obtained, which is a negligible difference, within the margin of error of most gauges used in the vessel's pressure range. It should be noted that this pressure drop and the membrane strains may actually be significantly less due to the Poisson effect. As the diaphragm will experience large compressive stresses through the thickness, these will tend to relieve the in-plane tension of the membrane stresses, possibly even overcompensating and leading to wrinkling of the diaphragm.

This system was designed primarily to conduct water ingression type accelerated life tests. Many polymers and polymer matrix composites (PMC's) have been known to respond negatively to long-term exposure to a marine environment, with significant degradation in mechanical properties being the norm. Diffusion of water into polymers under large hydrostatic pressures is a relatively well studied phenomenon, yet the effects on mechanical properties have not been well investigated. Additionally, due to the complications of pressurizing heated saline water that this system addresses, previous work has almost exclusively used pure, deionized water with the assumption that the added salt does not have an appreciable effect. A study was performed which investigated both the quasi-static and dynamic performance of carbon fiber/epoxy (CFE) PMC's after being subjected to sea-floor depth pressures for simulated time scales on the order of years.

First, a diffusion study was performed which characterized the temperature dependence of the diffusivity of water into the composite. Once high pressure absorption curves were obtained using a pressure vessel similar to one typically used and the temperature dependence was quantified, a quantity known as the acceleration factor, AF, was calculated, which related in-laboratory exposure time at elevated temperatures with real world service time at lower temperatures. For the specific PMC's used in this study, the acceleration factor was determined to be 0.64 yr/day when aged at a temperature of 70° C. and pressure of 41.3 MPa. Three weathering cases were chosen, an unweathered baseline, 14 days, and 24 days, equivalent to 0, 8.9 and 15.3 years of actual service, respectively.

Specimens were cut using a diamond saw to dimensions set forth in ASTM D3039 for tension coupons and ASTM D7264-15 for three-point bend coupons. Tensile tests were carried out in an Instron 5585 universal test frame equipped with a 250 kN load cell and taken to failure, while three-point bend tests were carried to 15 mm center deflection of a 20 cm span. The engineering stress-strain curves obtained are shown in FIGS. 4A, 4B, 4C and 4D. The tensile behavior of the composite was unchanged by aging, with a linear trend persisting until ultimate failure, as expected. However, flexural behavior was highly affected by moisture ingression, decreasing significantly as aging time increased. Further analysis of the stress-strain data enabled the calculation of the average tensile moduli, flexural moduli, and tensile stresses and strains at failure for the three weathering cases, given in Table 1.

TABLE 1

Results of In-Plane Tensile Tests

| Parameter | Unweathered | 14 Day | 24 Day |
|---|---|---|---|
| Tensile Modulus (GPa) | 71.87 | 73.00 | 72.56 |
| Flexural Modulus (GPa) | 13.9 | 12.1 | 11.0 |
| Maximum Tensile Stress (MPa) | 813 | 809 | 807 |
| Strain at Max Tensile Stress (%) | 1.03 | 1.13 | 1.20 |

Most notably, the tensile modulus was unchanged by weathering, the observed differences being within a 95% margin of error for each test, while flexural modulus decreased significantly, by 13.2% and 20.8% after 14 and 24 days of exposure, respectively. Due to the variability in general of failure of polymer-matrix composites, the differences in tensile failure stresses and strains are not statistically significant, and thus the common trend of increased degradation with aging was not present in tension during this high pressure study, though flexural properties degraded at similar rates to what would be expected. Although work is ongoing to further study this phenomenon, it is speculated that the large hydrostatic pressures, while aiding diffusion on a macroscopic level, closes voids at the matrix-fiber interface and forces the ingressed water to concentrate between plies, thus leaving the in-plane properties relatively unchanged. This result was unexpected and shows the importance of using this system for performing high pressure ALT.

Figure 5A:
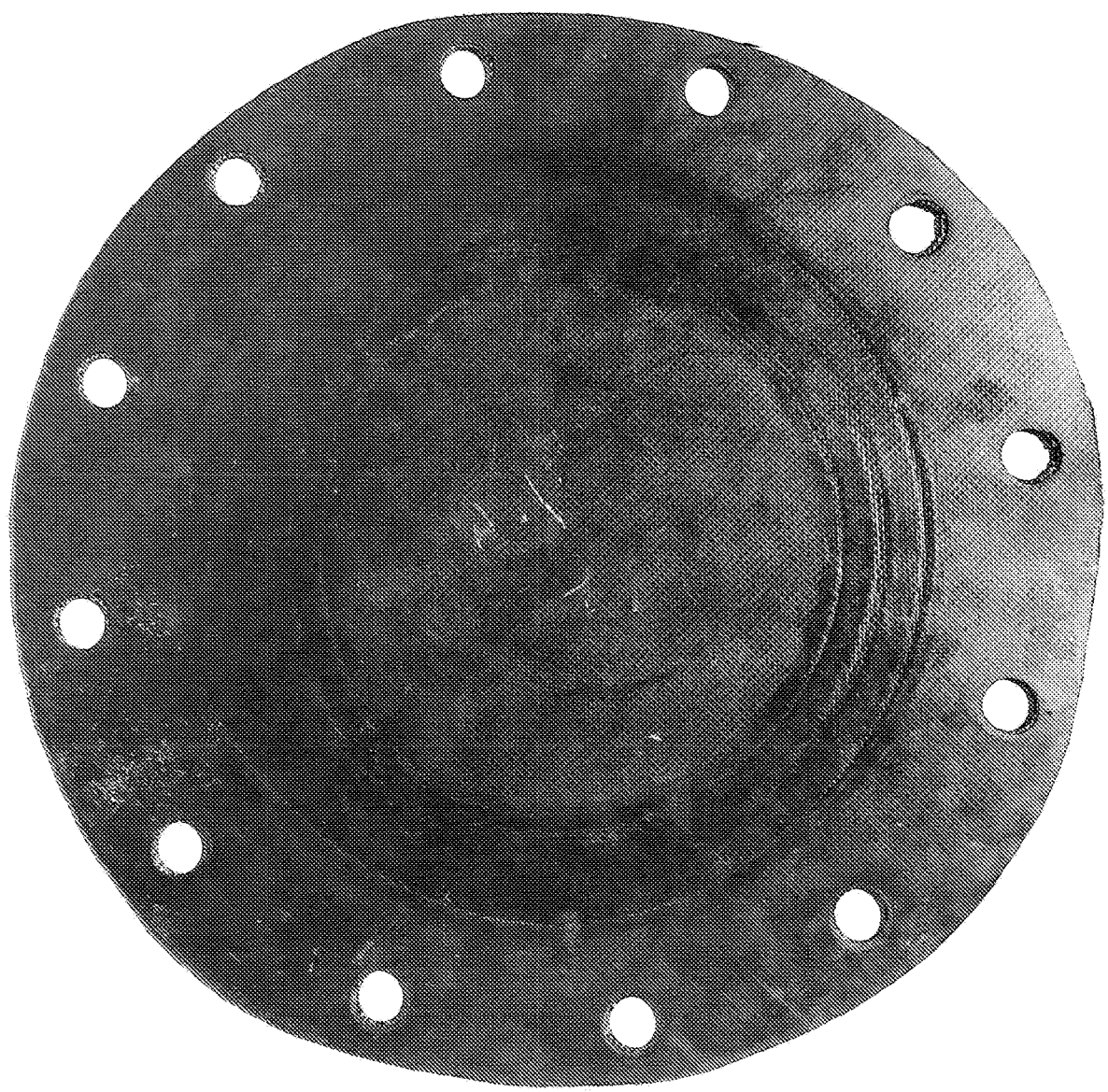
FIG. 5A is a photograph of the water side of a diaphragm that successfully held test pressure in a room temperature test.
Figure 5B:
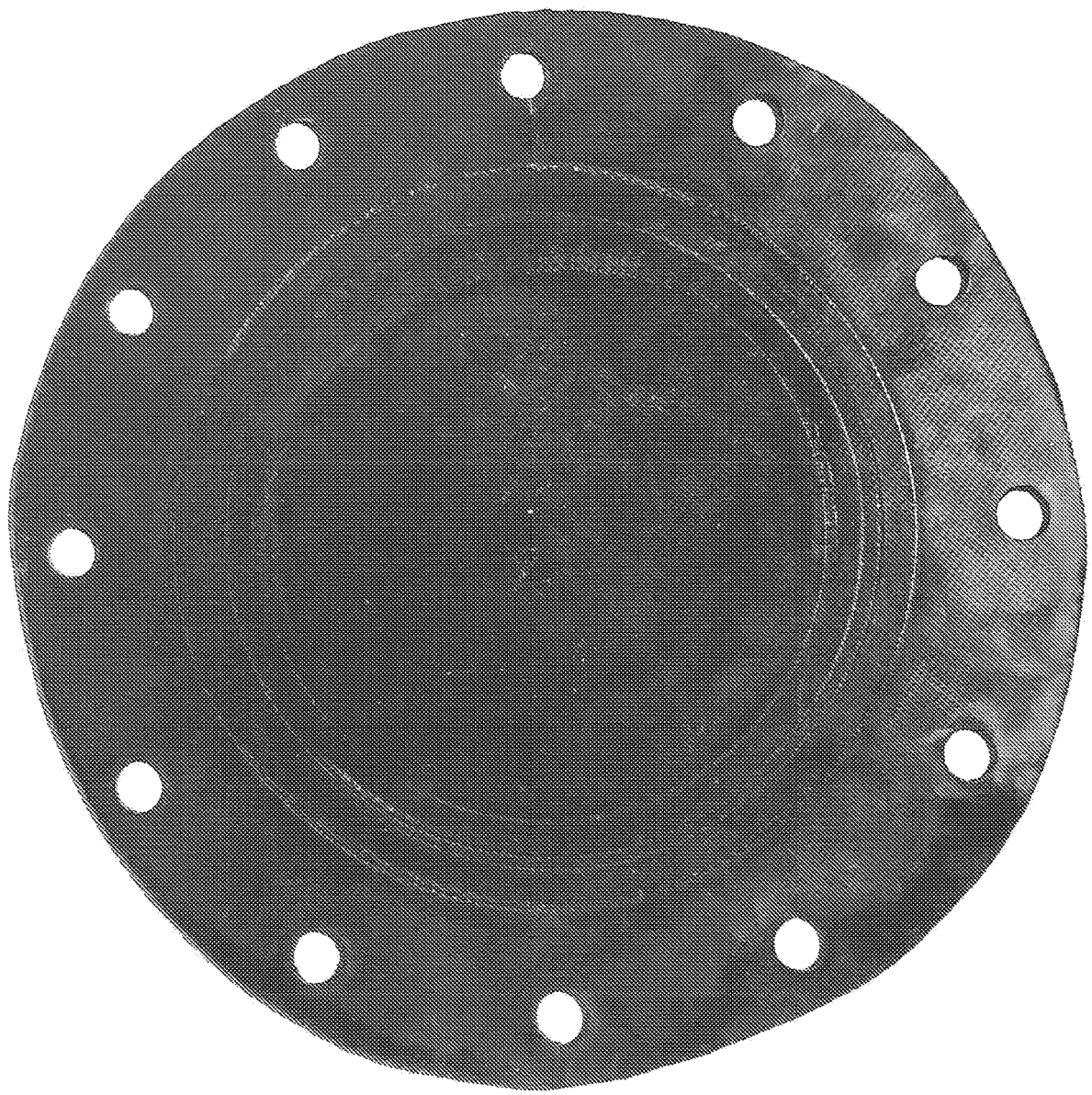
FIG. 5B is a photograph of the oil side of the diaphragm of FIG. 5A.
Figure 5C:
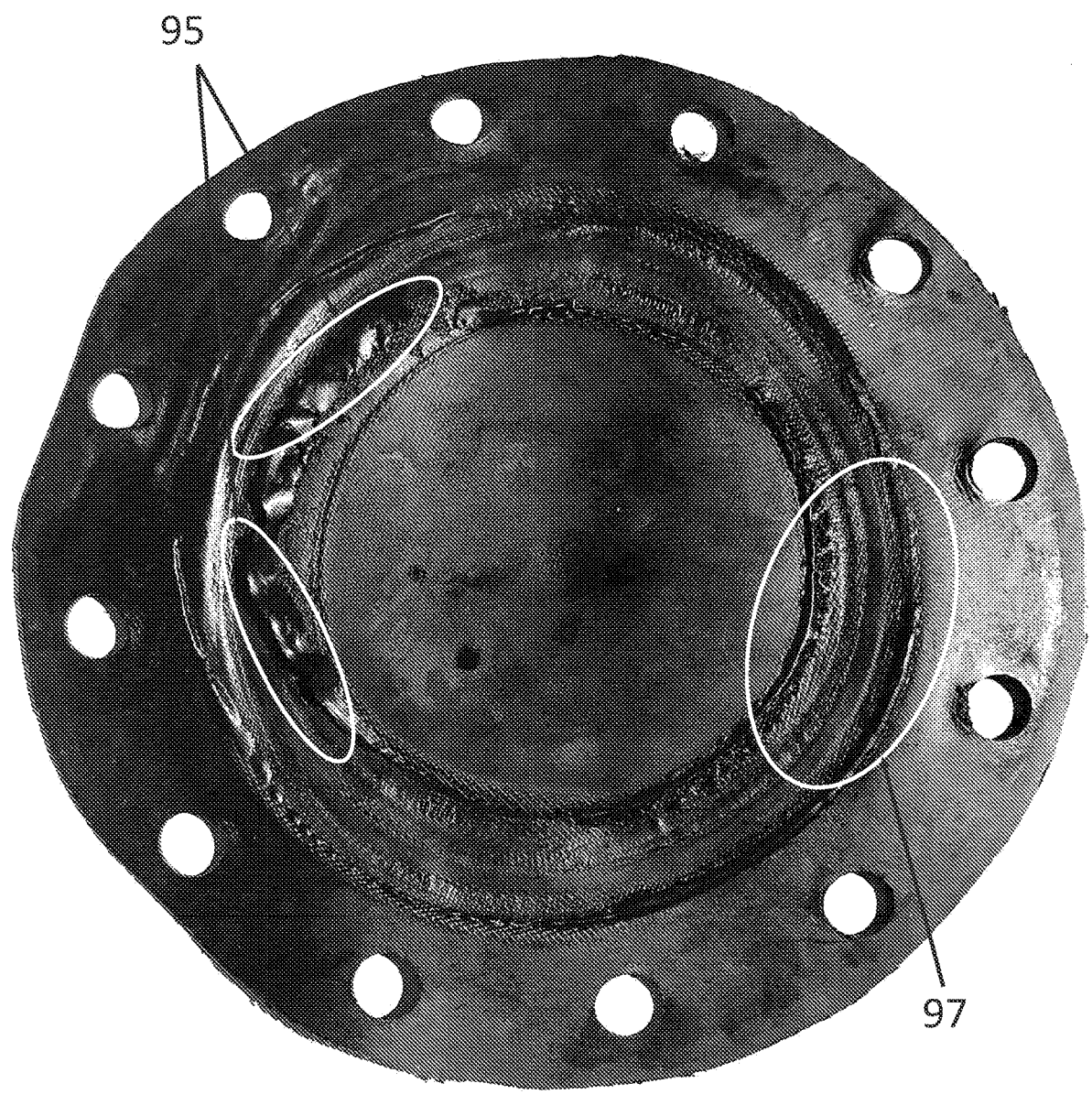
FIG. 5C is a photograph of the water side of a diaphragm that leaked at 35 MPa during a 65° C. test.
Figure 5D:
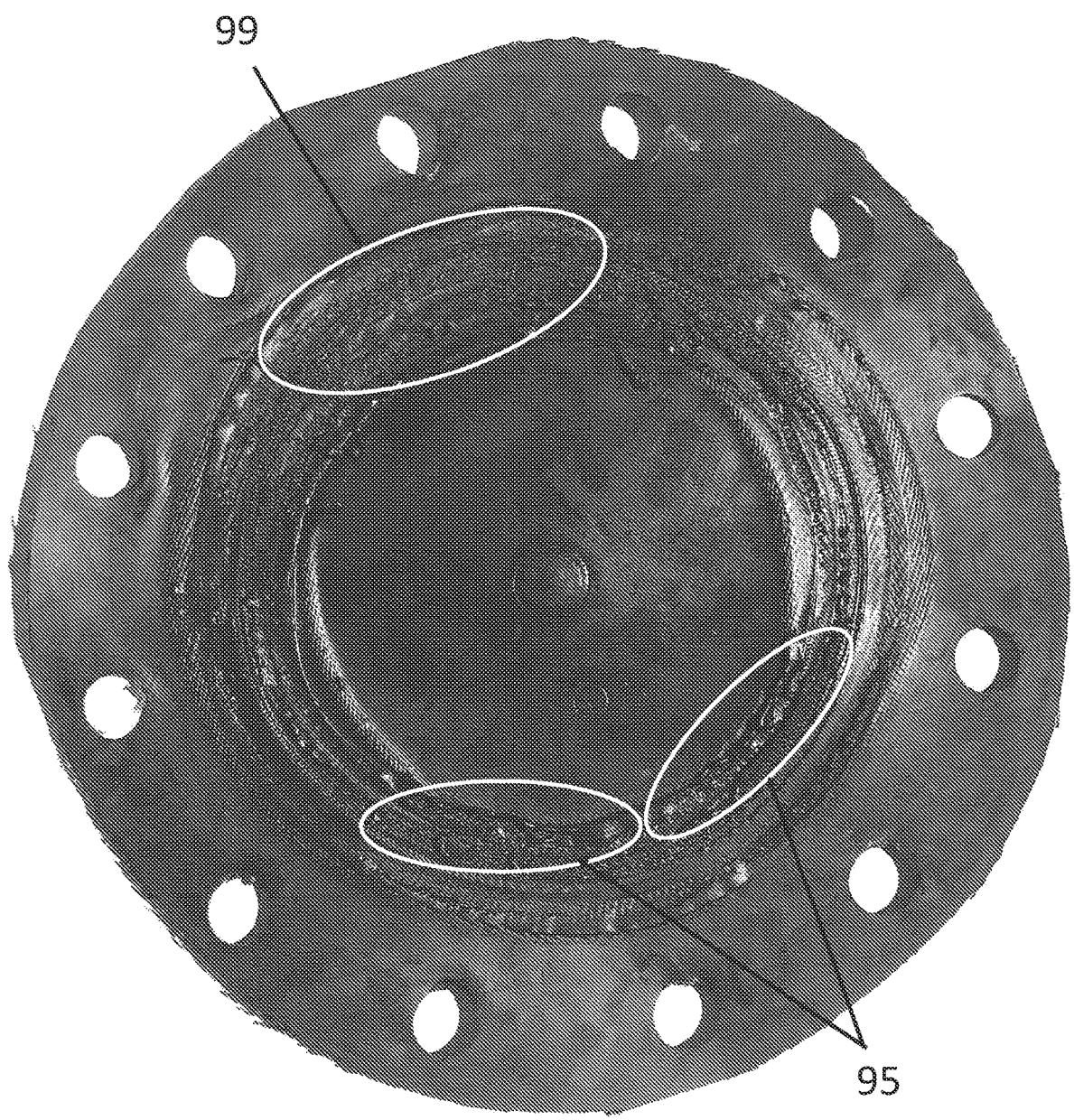
FIG. 5D is a photograph of the oil side of the diaphragm of FIG. 5C.

The diaphragm and O-ring seals, which comprise elastomers, are naturally sensitive to changing temperatures and thermocycling. Also, because the diaphragm is effectively a composite of nitrile and nylon, there are additional potential complications of delamination due to through-thickness stress and dissimilar rates of thermal expansion. The effects of temperature on the diaphragm can plainly be seen by comparing the two sample diaphragms shown in FIGS. 5A-5D, both of which saw similar pressures but at different temperatures. FIG. 5A is a photograph of the water side, and FIG. 5B is a photograph of the oil side, of a diaphragm that successfully held test pressure in a room temperature test. There is very little compression set and no visible extrusion. FIG. 5C is a photograph of the water side, and FIG. 5D is a photograph of the oil side, of a diaphragm that leaked at 35 MPa during a 65° C. test. The leakage was determined to be the result of catastrophic failure of the inner O-ring. Heavy extrusion and partial delamination of the outermost layer of rubber from the cloth can be seen at this location at 95 in FIG. 5C and FIG. 5D, suggesting that the problem was multifaceted. There is noticeable extrusion and delamination of the face layer at the edges of the clamping zone on the water side at 97. Though there is heavy extrusion into the O-ring glands on the oil side at 99, there is no penetration through the thickness. Raising the temperature softened the diaphragm material and increased the amount of extrusion into the oil-side O-ring glands. While the delamination was likely the result of the violent tearing nature of the failure, the extrusion of both diaphragm and O-ring material, which were both similar grades of nitrile, suggest thermal softening of both parts played a role. O-ring extrusion occurs in a face seal when the gap size between the faces reaches a critical size for the O-ring and pressure. A soft O-ring at higher pressures is much less tolerant of a gap than a hard O-ring at lower pressures. It is thought that because the flange was tightened at ambient temperature, as the temperature increased and both diaphragm and O-ring softened, the pressure was enough to open a gap between the now compliant diaphragm and lower end-cap, a gap the O-ring could not tolerate.

To counteract this problem, two modifications were implemented with success. Firstly, the nitrile O-rings were replaced with FKM O-rings of a higher durometer rating. FKM flouroelastomer O-rings are known to retain their stiffness better at higher temperatures, and the higher hardness was chosen to increase gap tolerance and lower the risk of extrusion. Additionally, the assembly procedure for the bottom seal was modified to incorporate pre-heating. The diaphragm and O-rings were installed as before at ambient temperatures and the bolts tightened, but then the entire vessel was heated to the maximum operating temperature of 70° C. and allowed to come to thermal equilibrium over the course of several hours. The vessel was empty during this time and any pressure caused by heating could release. Then the bolts were tightened to their torque specifications once again to take up the increased compliance of the diaphragm due to heating. A slight increase in the compliance was in fact noticed by the apparent loosening of the bolts before their retightening. Together, these two modifications proved successful in maintaining integrity of the seal, as the vessel was cycled several times and allowed to hold pressure for several days without issue before it was once again disassembled to check for any degradation of the diaphragm.

Figure 6:
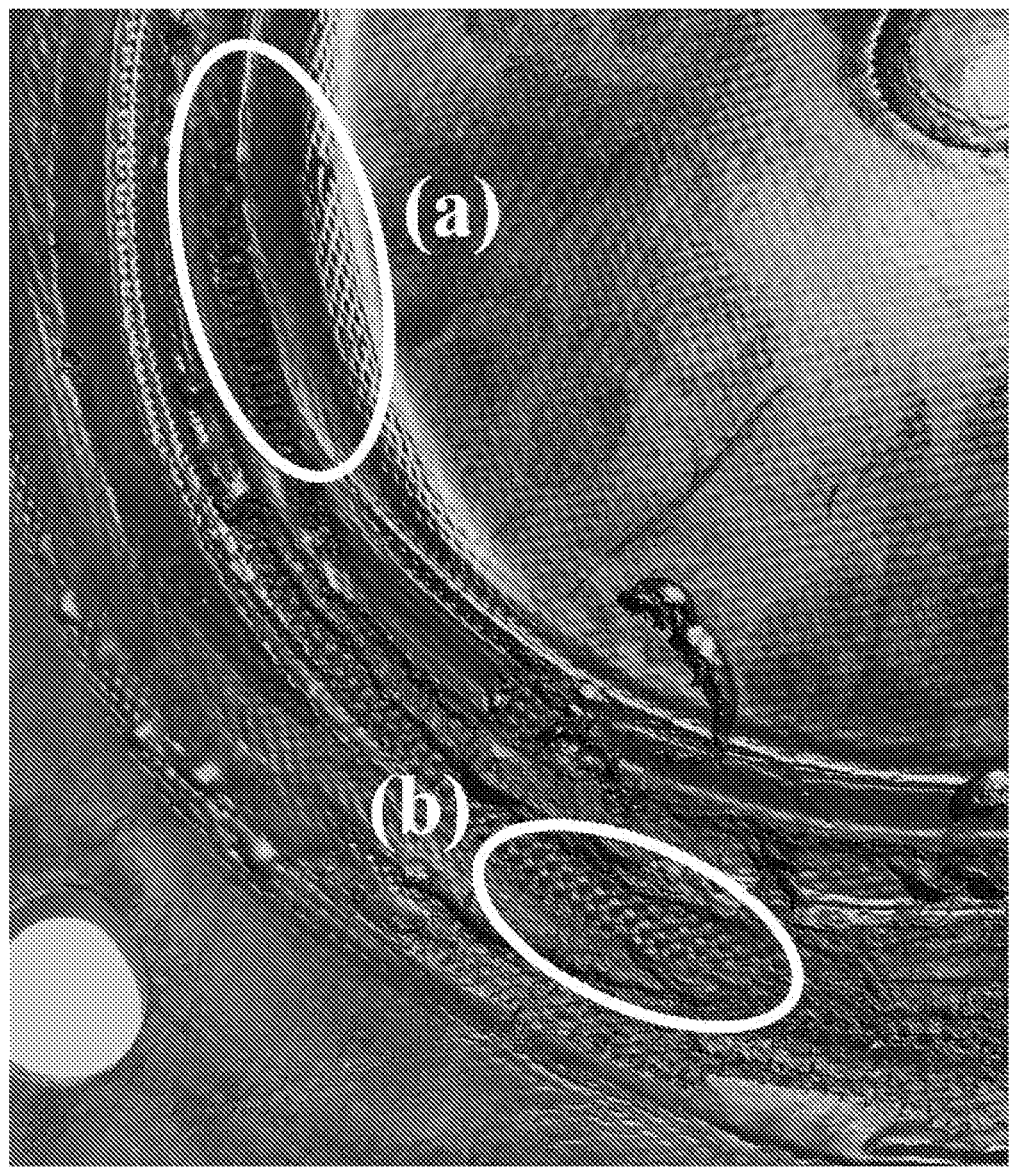
FIG. 6 is a detail of the photograph shown in FIG. 5D.

A detail of the diaphragm shown in FIG. 5D is shown in FIG. 6. The modes of degradation of this example serve as good examples of the types of deterioration that can occur in this system if proper countermeasures are not put into effect. The primary extrusion lobe can be seen at (a), where the diaphragm material begins to be forced into the inner O-ring gland. Moving outwards radially, some delamination of the outer rubber face from the lower cloth ply is seen. The severity of this delamination is most likely the result of the sudden failure of the O-ring and the large release of pressure that followed, and not from normal service. It should be noted that even with this delamination, only the outer face is affected; the core layer of rubber which is sandwiched between the two plies of cloth is undamaged, so the process media and pressurizing media remained isolated even after failure. More delamination is seen at (b), this time occurring over the secondary O-ring gland. Once again, only the outermost layer of rubber is affected, and the middle and top layers of rubber are not penetrated. The cause of this is thought to be the discontinuity in through-thickness compression at the edge of the O-ring gland combined with thermal softening of the nitrile. The compression on either side of the discontinuity combined with the Poisson effect most likely formed the softened rubber into a lobe or bubble, which was torn by the sudden friction of the extruding O-ring and the subsequent release of pressure.

Figure 7:
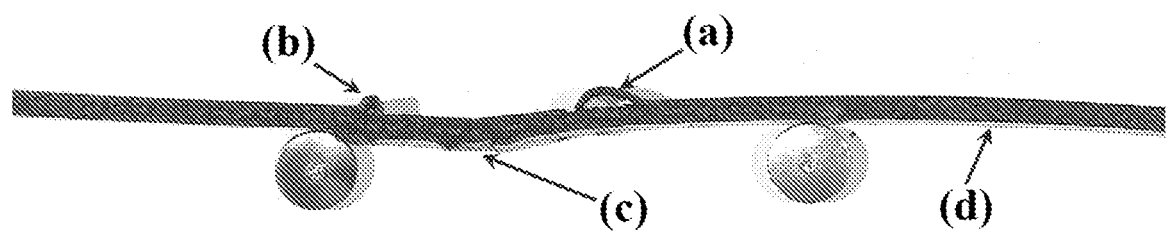
FIG. 7 is a cross-section of a diaphragm showing damage at the sealing locations.

Additionally, small amounts of delamination were observed on the water side, due to the clamping pressure of the body section against the lower end-cap. This can be seen in FIG. 7, a cross section of a diaphragm that leaked slightly after several hours of test pressure hold but did not fail catastrophically. A primary delamination lobe is seen at (a), where in-plane compression due to bending of the diaphragm into the water section combined with the through thickness pressure to cause some separation of the rubber face. Once again, the reinforcing nature of the cloth restricted the inner rubber layer from doing the same, and thus there was no through-thickness penetration. A similar phenomenon was observed on the outer edge of the seal at (b), although it is not as pronounced as at (a) due to the lack of pressure on the outlying portions of the diaphragm. The cloth is exposed in a similar manner as can be seen at (b) in FIG. 6. Additionally, extrusion at the O-ring glands can be seen in FIG. 7 at (c), but there does not appear to be delamination of the rubber at this location. On the interior portions of the diaphragm where the through-thickness stress is constant without discontinuities at the boundaries, seen at (d), the material is unaffected; the strength of the nylon cloth is enough to restrict the nitrile from extruding without delaminating.

In summary, most if not all damage to the diaphragm occurs at stress discontinuities at the boundaries of the water side seal and at the edges of the O-ring glands. The severity of the damage is heavily dependent on temperature and the softening of the nitrile at elevated temperatures. It is thought that hardening the nitrile at these locations, perhaps by a chemical treatment or the bonding of a hard polymer to the face layers, would significantly reduce the probability of this damage progressing and increase the reliability of the system as a whole.

Note that in the specification and claims, "about" or "approximately" means within twenty percent (20%) of the numerical amount cited. As used herein, the singular forms "a," "an," and "the" include plural referents unless the context clearly dictates otherwise. Thus, for example, reference to "a functional group" refers to one or more functional groups, and reference to "the method" includes reference to equivalent steps and methods that would be understood and appreciated by those skilled in the art, and so forth.

Although the invention has been described in detail with particular reference to the disclosed embodiments, other embodiments can achieve the same results. Variations and modifications of the present invention will be obvious to those skilled in the art and it is intended to cover all such modifications and equivalents. The entire disclosures of all patents and publications cited above are hereby incorporated by reference.

What is claimed is:

1. A system for pressurizing corrosive media, the system comprising:
    a vessel configured to contain a corrosive media and a test specimen;
    a flexible diaphragm, wherein a first side of said diaphragm is configured to seal one end of said vessel;
    a connection assembly configured to transport a pressurizing fluid to a second side of said diaphragm; and
    a temperature-controlled water bath configured to submerge said vessel.

2. The system of claim 1 wherein said vessel comprises stainless steel.

3. The system of claim 1 wherein an interior of said vessel is coated with a ceramic coating.

4. The system of claim 3 wherein said ceramic coating is a resin-based ceramic thin film coating.

5. The system of claim 1 comprising one or more hoisting rings configured to receive one or more hooks to lift said vessel into said water bath, the one or more hoisting rings attached to a top of said vessel.

6. The system of claim 1 comprising a pump configured to pressurize said pressurizing fluid against said second side of said diaphragm.

7. The system of claim 6 wherein said pump comprises a pressure release valve.

8. The system of claim 6 wherein said pump is connected to said connection assembly via a flexible hose.

9. The system of claim 6 wherein said diaphragm is configured to deform and protrude into said corrosive media when said pressurizing fluid is pressurized by said pump, thereby pressurizing said corrosive media to approximately a same pressure as the pressurized pressurizing fluid.

10. The system of claim 1 wherein said connection assembly comprises a rupture disc.

11. The system of claim 1 wherein said connection assembly comprises a pressure sensor.

12. The system of claim 11 wherein said pressure sensor is connected to said connection assembly via a flexible tube.

13. The system of claim 1 wherein said diaphragm comprises fabric reinforced nitrile rubber.

14. The system of claim 1 wherein said pressurizing fluid comprises hydraulic oil.

15. The system of claim 1 wherein said vessel is cylindrical.

16. The system of claim 15 wherein said diaphragm is clamped between a flange attached to said vessel and a bottom end cap, said flange and said bottom end cap having diameters greater than a diameter of said vessel.

17. The system of claim 16 wherein said flange is clampable to said bottom end cap using a plurality of through bolts.

18. The system of claim 16 wherein said bottom end cap comprises grooves for receiving one or more flouroelastomer O-rings configured to contain said pressurizing fluid between said second side of said diaphragm and said bottom end cap.

19. The system of claim 1 capable of maintaining said corrosive media at a pressure of approximately 6000 psi and at a temperature greater than approximately 40° C. for more than approximately one month without corrosive failure of the system.

20. The system of claim 1 capable of maintaining said corrosive media at a pressure of approximately 6000 psi and at a temperature greater than approximately 40° C. for more than approximately three months without corrosive failure of the system.

21. The system of claim 1 wherein said corrosive media comprises seawater, saline, or salt water.

22. The system of claim 1 capable of performing accelerated life testing (ALT) of said specimen.

* * * * *